United States Patent [19]

Allen, III

[11] 4,009,496

[45] Mar. 1, 1977

[54] PROSTHETIC ADAPTER FOR SKI POLES AND THE LIKE

[76] Inventor: Ralph Samuel Allen, III, 1610 Dahlia St., Denver, Colo. 80220

[22] Filed: May 24, 1976

[21] Appl. No.: 689,468

[52] U.S. Cl. .......................... 3/12.8; 280/11.37 E; 280/11.37 H; 16/110 R
[51] Int. Cl.² .......................................... A61F 1/06
[58] Field of Search ........................... 3/12.8, 12, 1; 280/11.37 R, 11.37 H, 11.37 E, 11.37 J, 11.37 L, 11.37 T, 11.37 B, 11.37 D; 16/110 R, 127

[56] References Cited

UNITED STATES PATENTS

| | | | |
|---|---|---|---|
| 2,566,215 | 8/1951 | Croix | 3/12.8 |
| 3,036,312 | 5/1962 | Larsen et al. | 3/12.8 |
| 3,179,435 | 4/1965 | Miller | 280/11.37 H |
| 3,738,674 | 6/1973 | Pauls | 280/11.37 B |

Primary Examiner—Ronald L. Frinks
Attorney, Agent, or Firm—John E. Reilly

[57] ABSTRACT

A prosthetic adapter has been devised which is conformable for use by amputees in various activities without necessity of modifying the prosthesis or artificial limb itself. This is achieved by utilization of diametrically opposed connectors on a grip or handle portion of the article to be manipulated, the fasteners preferably being offset one from another for a distance corresponding to the offset relation of the hook portions on the artificial hand. In those applications where the article is to be freely suspended, such as, a ski pole, a resilient connector is employed in combination with the diametrically opposed connectors for releasable attachment of another hook so that the vertical attitude or disposition of the pole can be regulated.

11 Claims, 4 Drawing Figures

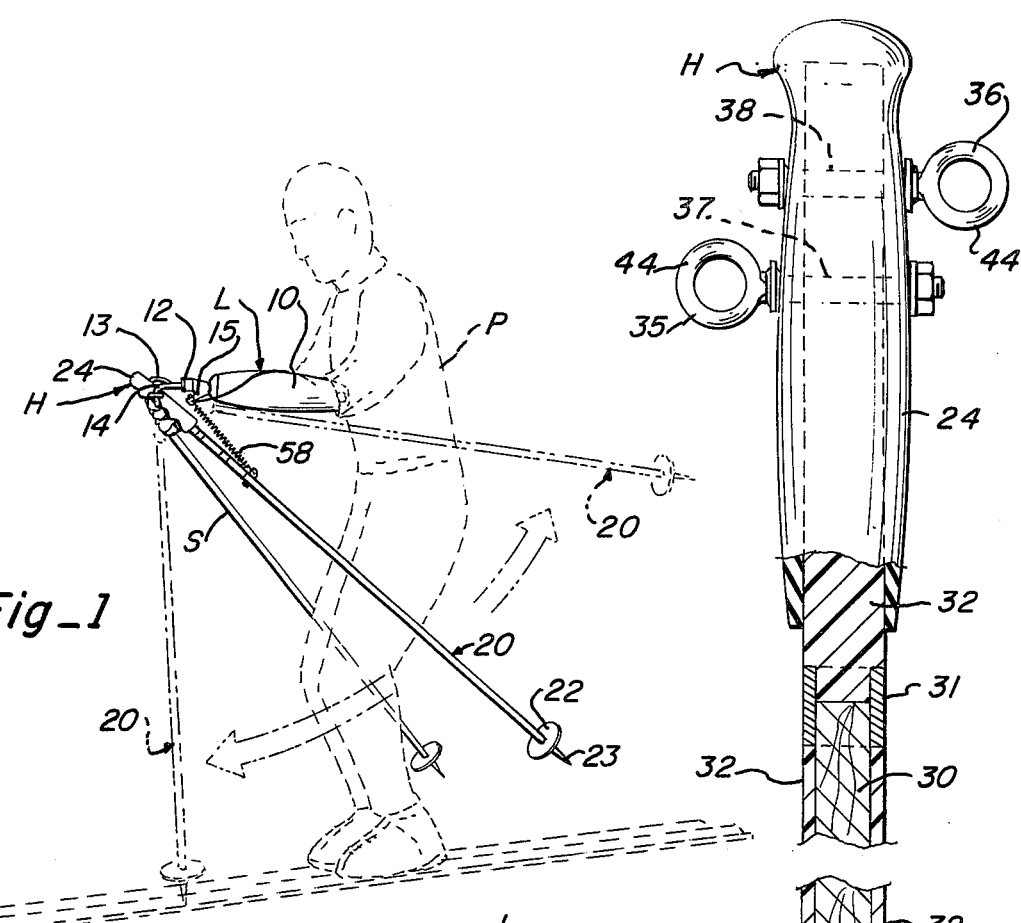
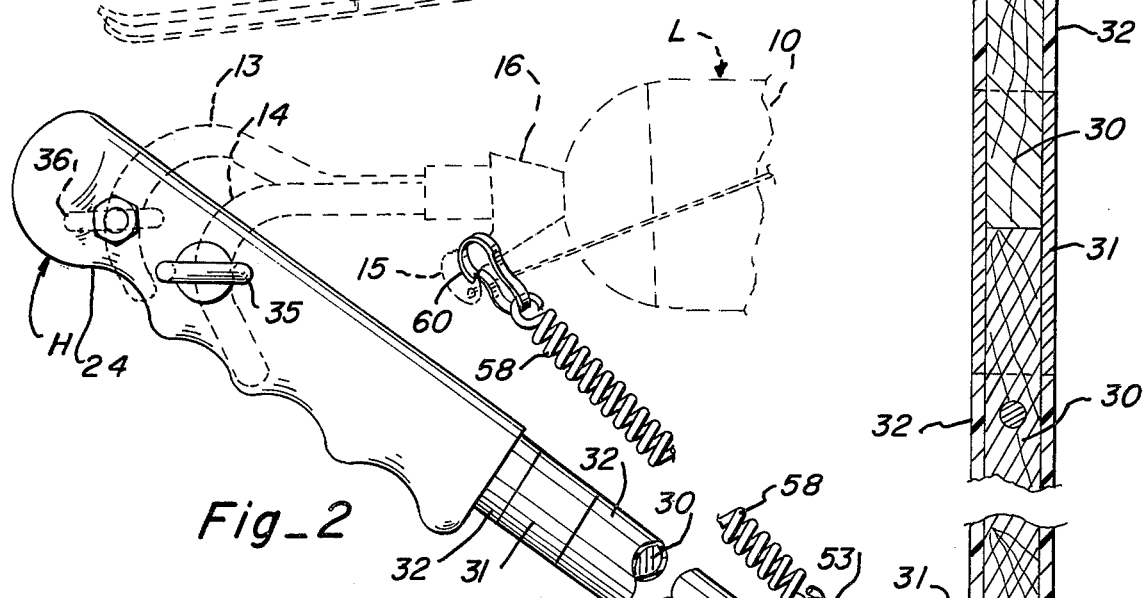
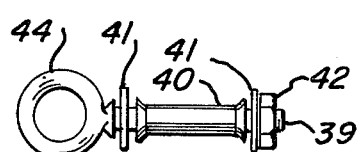
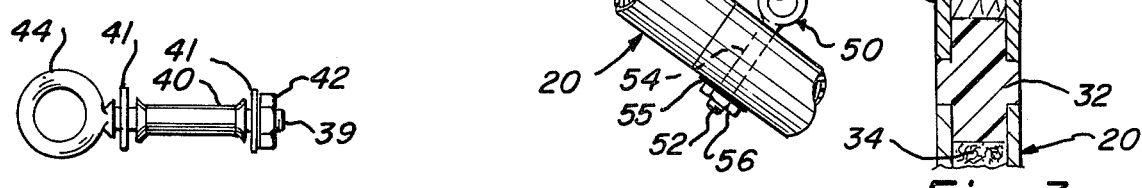
Fig_1  Fig_2  Fig_4  Fig_3

PROSTHETIC ADAPTER FOR SKI POLES AND THE LIKE

BACKGROUND OF THE INVENTION

This invention relates to prosthetic devices and particularly relates to adapters for artificial limbs, specifically the hand, to permit releasable attachment and manipulation of the article by an amputee.

Customarily, an amputee who has lost one or both hands is fitted with an artificial arm component together with an artificial hand, the latter conventionally comprised of an upper pair of metallic hooks and a lower spaced artificial hook interconnected in such a way to permit the person to carry out various activities. However, due to the limited degree of movement and control afforded over hook portions, the artificial hand is limited in the performance of certain activities. This is particularly so with respect to manipulation or control of elongated articles, such as, for instance, ski poles, rifles or the gear shift or steering wheel on a car.

In order to enable the amputee to carry out certain special activities, such as, athletics, the approach generally taken in the past has been to modify the construction of the artificial hand or limb itself according to the specific application. Generally representative of approaches taken in the past in U.S. Pat. No. 3,738,674 to Pauls which discloses a special skiing device for a handicapped person in the form of an arm crutch equipped with a lower ski portion convertible for use in walking. Similarly, the patent to Katz U.S. Pat. No. 3,656,187, makes provision for a specially formed artificial hand adapted for violin playing. Other adapter arrangements for artificial hands to operate and manipulate various devices are known, for instance, U.S. Pat. No. 2,561,523 to Lux discloses a tool attachment capable of producing a wrist-like action for use in activities such as sweeping, raking or similar chores involving implements employing a handle portion. The patent to La Croix, U.S. Pat. No. 2,566,215, also discloses a wrist adapter for tennis rackets which is secured to an artificial limb in such a way as to facilitate sturdy but flexible movement of the adapter. Other patents of interest for disclosing prosthetic devices are Larsen et al. U.S. Pat. No. 3,036,312 and De Filipo U.S. Pat. No. 3,747,128. To the best of my knowledge however no one has devised a prosthetic device in the form of an adapter which is conformable for use in various activities without modification of the artificial limb or hand itself and in such a way as to permit detachable engagement by the prosthesis to control linear and rotary movement of an article.

It is therefore an object of the present invention to provide for a novel and improved adapter for artificial hands which permits releasable engagement and control of the article without modification of the artificial hand itself.

Another object of the present invention is to provide a novel and improved prosthetic device which is particularly useful for engagement with and control of the grip end of handle of articles such as a ski pole, rifle, gear shift or steering wheel on a car.

SUMMARY OF THE INVENTION

The above and other objects and features are realized in accordance with the present invention by an adapter which permits releasable attachment of an artificial hand wherein the hand conventionally includes spaced hook portions. The present invention is best exemplified by describing its use in connection with a ski pole wherein diametrically opposed connectors or fasteners are journaled to opposite sides of the grip or handle portion of the pole, the fasteners preferably being longitudinally offset from one another for a distance corresponding to the offset relation of the upper hook portions to one another when spread apart. A third connector is affixed to the handle normal or perpendicular to the first and second connector including a resilient extension for releasable attachment of a lower hook on the artificial hand so that the skier can readily attach the upper hooks on the upper portion of the handle into the first and second connectors and attach the lower hook to the resilient connector in such a way as to regulate the vertical attitude or disposition of the ski pole. Thus, in skiing, the pole will normally be urged to assume a slight rearward angle when not planted in the snow thereby assuring that the poles will not interfere with the skier in executing various turns on a ski slope; yet can be positively manipulated and be firmly planted in the snow when desired as an aid in imparting a forward thrust or executing particular turns requiring assistance of the pole.

BRIEF DESCRIPTION OF THE DRAWING

Other objects, advantages and capabilities of the present invention will be more readily apparent when taken in conjunction with the detailed description and drawings.

FIG. 1 is a somewhat perspective view of a skier with the prosthetic device of the present invention attached to a ski pole.

FIG. 2 is a view partially in section of the handle portion of a ski pole.

FIG. 3 is another view of the upper grip portion of a ski pole; and

FIG. 4 is a view in detail of one of the connectors employed in association with the ski pole.

DETAILED DESCRIPTION OF THE PREFERRED EMBODIMENT

Referring in detail to the drawings, there is shown by way of illustrative example in FIG. 1, a conventional form of ski pole S having a modified form of handle H embodying the adapter 10 of the present invention so that the pole is conformable for use by an amputee generally designated at P. As a setting for the present invention, a conventional artificial limb is represented at L including a forearm portion 10 and a hand component 12, the latter consisting of a pair of forwardly extended upper hook portions 13 and 14 together with a lower spaced hook portion 15. As shown in more detail in FIG. 2, the hooks 13 and 14 on the artificial hand are secured to a common yoke 16, each of the hooks being of generally L-shaped configuration so as to project forwardly and slightly downwardly from the yoke, one hook 13 being laterally pivotal with respect to the hook 14. It is also customary for the stationary hook 14 to have a slightly greater curvature or bend at its end than the pivotal hook 13. In addition, the lower hook portion 15 is connected to pivot with the hook 13, and some spring tension may be exerted such as by means of a rubber band, not shown, so as to be normally retained by the hooks 13 and 14 together. It is emphasized that other types of prosthesis have been devised for use as artificial hand but all with slight modifications are generally characterized by a plurality of hook portions which are capable of undergoing limited pivotal movement with respect to one another.

In the preferred embodiment of the present invention, and as best seen from a consideration of FIGS. 1 to 4, a standard ski pole as represented in FIG. 1 has an elongated tubular section 20 the upper end of which defines the handle portion H and a lower end provided with a basket 22 directly above the lower pointed extremity 23 so that penetration of the pole into the snow is limited by the basket 22. In turn, a rubber grip 24 is placed over the end of the handle H so as to permit gripping or grasping by the hand in normal use.

In accordance with the present invention, as shown in more detail in FIGS. 2 to 4, the ski pole S is modified in the following manner: The upper end of the tubing section 20 adjacent to the handle H is severed to permit insertion of a wood dowel 30 having outer surrounding tubing portions 31 at spaced intervals for snug-fitting insertion into the severed portions of the tubing 20. The wood dowel is anchored to splice the severed portions of the tubing section together by means of a suitable bonding and fill agent, such as, a polyester resin generally designated at 32. Specifically the resin may entirely fill the extreme end of the tubing section within the grip 24 and flow into surrounding relation to the dowel 30 and between the tubular portions 31. A suitable plug which may typically be composed of cotton and represented at 34 is inserted at the lower end of the dowel merely to limit the flow of the resin and retain it in place until it hardens and securely unites the dowel 30 and tube portions 31 to the inner wall of the tubing section. Eye-bolts 35 and 36 are inserted through transverse bores 37 and 38, respectively at the upper end of the grip 24, each eye-bolt correspondingly including a threaded portion 39 which projects through a sleeve 40 inserted into each of the bores 37 and 38 with washers 41 positioned on the threaded portion 39 at opposite ends of the sleeve together with a lock nut 42. Each eye-bolt includes an eye or ring-shaped end portion 44 which is sized to permit insertion of one of the hooks 13 or 14. It will be noted that the bores 37 and 38 are disposed in adjacent but offset relation to one another so as to extend transversely through the grip, and the eye-bolts 35 and 36 are journaled in the bores as described with the ring portions 44 located on opposite sides of the grip, their longitudinal spacing corresponding to the spacing between the hooks 13 and 14. For example, FIG. 3 illustrates this relationship for the right hand prosthesis where the hook 13 is pivotal with respect to the hook 14 and is shorter than the hook 14. The eye-bolt connection as described serves as a simplied, highly effective means of permitting manipulation and control of the pole when the fingers are inserted therethrough, since the generally L- or J-shaped configuration of the hooks will permit limited turning of the pole about its longitudinal axis as well as some degree of swinging movement through a vertical plane.

A lower hook connector is provided on the ski pole S in order to permit close control over normal attitude or disposition of the pole when in use, the connector being defined by an eye-bolt 50 inserted through a transverse bore formed in the tubing section in a direction normal to the direction of extension of the bores 37 and 38. The eye-bolt 50 includes a threaded portion 52 terminating at one end in an eye 53 and is journaled in the bore by a suitable sleeve 54 and locked in place by a washer 55 and nut 56 with the eye projecting from the upper surface of the tubing section in somewhat spaced relation beneath the grip 24. In order to serve as a means of resilient connection for the hook 15, a coiled spring member 58 is attached at one end to the eye and extends upwardly to terminate in a spring clip 60 at its opposite free end whereby to permit insertion of the end of the hook 15.

In connected relation to the hook 15 and assuming that the hooks 13 and 14 are inserted through the eyes 44 in the manner previously described, the normal attitude or disposition of the pole is as shown in full in FIG. 1 so as to incline somewhat rearwardly with respect to the direction of the skier thereby to avoid or minimize any tendency to interfere with or impede the movement of the skier. However through pressure exerted upon the upper eye-bolts, or by swinging the pole S forwardly, the skier may cause the poles to advance into a more nearly vertical position, as shown dotted in FIG. 1, for example when it is desired to plant the ski poles in the snow and to impart forward thrust. As the skier advances forwardly under the forward thrust imparted, the ski poles will once again return to their rearwardly inclined position as shown in full, or may be raised to a more nearly horizontal position.

If desired, and in accordance with conventional practice, rubber tubing or tape may be placed on the prosthetic hooks 13 and 14 to more securely retain them in place within the eyes 44 with the clip 50 being more positively attached to the hook 15. The spring tension in the spring 58 is such as to normally incline the pole as described but can be easily overcome by manipulation of the pole.

It will be readily apparent that the eye-bolts 35 and 36 may be employed independently of the thumb connector as described to permit manipulation of the ski pole. However, the thumb connector lends a substantial degree of safety to use of the pole in maintaining the pole in a rearwardly inclined attitude. In this relation, the offset eye-bolts are readily conformable for use in other applications to provide a positive, but releasable, means of engagement for the hooks and in such a way as to facilitate grasping and control of various articles by amputees. Typical applications would be for use in connection with gear shifts, steering wheels or various athletic equipment. Most notably the adapter as hereinbefore described permits releasable attachment of conventional prosthesis or artificial hands without modification of the artificial hand itself.

It is therefore to be understood that various modifications and changes may be made in the specific construction and arrangement of parts comprising the present invention without departing from the spirit and scope thereof as defined by the appended claims.

What is claimed is:

1. In a prosthetic device adapted for releasable attachment of an artificial hand to an article having an elongated handle portion wherein the artificial hand includes spaced hook portions, said prosthetic device comprising a pair of generally loop-shaped first and second fasteners disposed on opposite sides of the handle, each fastener being sized to provide an opening therein adapted for insertion of one of the hooks on the artificial hand, each of said fasteners including connector means for connecting said fastener to the handle in spaced offset relation to the connector means for said other fastener.

2. In a prosthetic device according to claim 1, said connecting means for each fastener being secured in journaled relation to said handle to permit turning of said fastener with respect to said handle.

3. In a prosthetic device according to claim 1, further including a third fastener affixed to said handle in spaced relation to said first and second fasteners, said third connector including resilient connector means yieldably interconnecting one of said hook portions on the hand to said handle portion.

4. In a prosthetic device according to claim 3, said third fastener further including connecting means inserted through said handle normal to the direction of extension of said first and second fasteners.

5. In a prosthetic device according to claim 1, each of said first and second fasteners defined by an eye-bolt extending transversely through the handle in longitudinally spaced relation to one another.

6. A prosthetic adapter for manipulating elongated articles of the type characterized by having a gripping portion thereon, said adapter comprising a pair of fastener means extending transversely through the handle in longitudinally spaced relation to one another, each of said fastener means including generally ring-like openings disposed on opposite sides of the handle, and a third fastener extending through said handle normal and in spaced relation to said first and second fastener.

7. A prosthetic adapter according to claim 6, each of said fasteners being defined by an eye-bolt mounted in journaled relation to the handle.

8. A prosthetic adapter according to claim 7, said third fastener including resilient connecting means thereon.

9. A prosthetic adapter for ski poles wherein the ski pole is characterized by having an elongated tubing section terminating at one end in a handle grip portion, said adapter being adapted for releasable attachment of an artificial hand to the ski pole wherein the hand includes upper spaced hooks and a lower spaced hook portion, said adapter comprising a pair of generally loop-shaped fasteners disposed on opposite sides of the handle grip of the pole, each fastener including a loop portion sized to provide an opening therein adapted for insertion of an upper hook on the artificial hand, and a third fastener secured to said ski pole in longitudinally spaced relation beneath said handle grip, said third fastener including a resilient connector adapted for releasable engagement with the lower spaced hook portion of the hand.

10. A prosthetic adapter according to claim 9, each of said fastener members being defined by eye-bolts secured in journaled relation to the ski pole.

11. A prosthetic adapter according to claim 9, a solid insert being disposed in the handle grip portion of said ski pole to reinforce the mounting and disposition of said fastener therein.

* * * * *